United States Patent [19]

Kawashima et al.

[11] Patent Number: 5,254,198
[45] Date of Patent: Oct. 19, 1993

[54] METHOD OF BONDING A METAL OR ALLOY UTILIZING A POLYMERIZABLE THIOCARBOXYLIC ACID OR A DERIVATIVE THEREOF

[75] Inventors: Mitsunobu Kawashima; Ikuo Omura, both of Kurashiki, Japan

[73] Assignee: Kuraray Co., Ltd., Kurashiki, Japan

[21] Appl. No.: 892,928

[22] Filed: Jun. 3, 1992

Related U.S. Application Data

[62] Division of Ser. No. 662,513, Feb. 28, 1991, Pat. No. 5,186,783, which is a division of Ser. No. 368,799, Jun. 20, 1989, abandoned.

[30] Foreign Application Priority Data

Jun. 20, 1988 [JP] Japan ................................. 63-152491
Aug. 8, 1988 [JP] Japan ................................. 63-198623

[51] Int. Cl.$^5$ ............................................... C09J 5/02
[52] U.S. Cl. ............................... 156/307.3; 526/286
[58] Field of Search ............... 156/307.3, 327, 331.1

[56] References Cited

U.S. PATENT DOCUMENTS 3,700,647 10/1972 Nakaguchi .
4,537,667 8/1985 Bishop .

*Primary Examiner*—Christopher Henderson
*Attorney, Agent, or Firm*—Oblon, Spivak, McClelland, Maier & Neustadt

[57] ABSTRACT

An adhesive composition comprising a polymerizable thiocarboxylic acid or a derivative thereof of the general formula $$R_1-\overset{\overset{X_1}{\|}}{C}-R_2$$

wherein $X_1$ is an oxygen atom or a sulfur atom and where $X_1$ is an oxygen atom, $R_1$ is an organic group containing at least one olefinic double bond and $R_2$ is a mercapto group, and where $X_1$ is a sulfur atom, $R_1$ is an organic group and $R_2$ is a mercapto group, a halogen atom, —$OR_3$, or —$SR_3$, where $R_3$ is a monovalent organic group, and at least one of $R_1$ and $R_3$ has at least one olefinic double bond, are useful as primers or adhesives and provide a water-resistant, high-strength bond to noble metal adherends which are used in dental and other applications.

1 Claim, No Drawings

METHOD OF BONDING A METAL OR ALLOY UTILIZING A POLYMERIZABLE THIOCARBOXYLIC ACID OR A DERIVATIVE THEREOF

This is a division of application Ser. No. 07/662,513, filed on Feb. 28, 1991 now U.S. Pat. No. 5,186,783, which is a division of application Ser. No. 07/368,799, filed on Jun. 20, 1989, now abandoned.

BACKGROUND OF THE INVENTION

1. Field of the Invention

The present invention relates to adhesive compositions which provide a high bond strength to metals and particularly to noble metals, a method of bonding metals using such an adhesive, and articles in which a metal is bonded using such an adhesive. More particularly, the present invention relates to adhesive compositions which provide a high bond strength to various metals used in the dental field.

2. Description of the Background

Adhesives based on monomers such as acrylic compounds and epoxy compounds can be allowed to cure at room temperature and atmospheric pressure in short periods of time, offering good workability, and as such have been in prevalent use for the bonding of metals. However, depending on the intended use, these adhesives may exhibit serious drawbacks. Thus, if the bonded product is kept exposed to water, the bond strength suffers a sharp decline, so that these adhesives can hardly be used in applications demanding water resistance.

Recently, in the field of dental materials, various attempts have been made to provide adhesives for metals with improved bond strength water resistance, and these efforts have been rewarded by some degrees of success. For example, a dental adhesive composition containing a phosphoric acid ester compound as disclosed in Japanese laid-open Patent Application Kokai No. 21607/1983 exhibits an excellent water-resistant bond strength to base metals, such as iron, nickel, chromium, cobalt, tin, aluminum, copper, titanium, etc., and base metal alloys containing such elements as major ingredients, and has actually been in use clinically as a dental cement. However, the adhesive composition according to this reference is inferior in the water resistance of the bond strength to noble metal alloys containing gold, platinum, palladium or silver, e.g. inlays, crowns and bridges, as compared to that to base metal alloys.

It has been therefore found necessary, for imparting an adequate water resistance of bond strength, that such noble metal alloy products should be surface-treated by tin plating or oxidation.

It was recently reported in the *Japanese Society for Dental Materials and Devices*, 5, 92–105 (1986) that coating of N-(4-mercaptophenyl)methacrylamide as a primer to a noble metal markedly improved the water resistance of adhesion of MMA-TBB resin to the noble metal.

Further, Japanese laid-open Patent Application Kokai No. 110523/1976 describes that a varnish based on a methacrylic acid ester is improved in its bond strength to a glass or an aluminum plate by addition of 3-(isopropenylthiocarbonylthio)propyltrimethoxysilane to the varnish. However, when the adhesive containing 3-(isopropenylthiocarbonylthio)propyltrimethoxysilane is applied to noble metals or noble metal alloys, the resulting bond strength is not sufficient for practical use.

As mentioned above, when a noble metal or its alloy is bonded to the tooth or a dental material with the adhesive disclosed in Japanese laid-open Patent Application Kokai No. 21607/1983, the metal surface must be previously treated by tin plating or oxidation and such a procedure requires skill and is time-consuming. This trouble can be obviated by using, instead, the above-mentioned N-(4-mercaptophenyl)methacrylamide-containing adhesive, but there still remains the problem that the water resistance of the adhesion is not adequate for practical use.

Thus, there remains a need for a primer for the surface conditioning of metals, particularly noble metals, prior to adhesion of a metal to another metal or other material which results in a high bond strength with a high water resistance, and there also remains a need for an adhesive for metal-to-metal bonding or metal-to-other material bonding which provides a high bond strength with a high water resistance.

SUMMARY OF THE INVENTION

It is, therefore, an object of the present invention to provide an improved primer for use in the surface conditioning of metals, particularly noble metals, prior to adhesion of a metal to a metal or other material.

It is another object of the present invention to provide an improved adhesive for metal-to-metal bonding or metal-to-other material bonding, which results in a high bond strength with a high water resistance. In this specification, both the primer and the adhesive are collectively referred to as "adhesive" or "adhesive composition".

It is another object of the present invention to provide a method of bonding a metal to another metal or other material using an adhesive or primer which results in a high bond strength having a high water resistance.

It is another object of the present invention to provide articles in which a metal is bonded to another metal or other material with an adhesive which results in a high bond strength having a high water resistance.

These and other objects which will become apparent during the course of the following detailed description have been accomplished by adhesive compositions containing a polymerizable thiocarboxylic acid or a derivative thereof of the general formula (I)

wherein $X_1$ is an oxygen atom or a sulfur atom and when $X_1$ is an oxygen atom, $R_1$ is an organic group having at least one olefinic double bond and $R_2$ is a mercapto group, while when $X_1$ is a sulfur atom, $R_1$ is an organic group, $R_2$ is a mercapto group, a halogen atom, $-OR_3$ or $-SR_3$, where $R_3$ is a monovalent organic group and at least one of $R_1$ and $R_3$ has at least one olefinic double bond.

DETAILED DESCRIPTION OF THE PREFERRED EMBODIMENTS

One aspect of the present invention resides in the use of a compound of the above general formula [I] (which will hereinafter sometimes be referred to as the present compound).

The compound of general formula [I] is characterized by the moiety

As specific examples of the

group, there may be mentioned

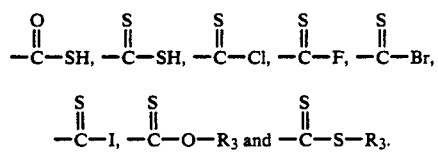

In the present specification, a compound having any of these groups are called a thiocarboxylic acid or a derivative thereof.

Furthermore, the term "olefinic double bond" as used in the present specification means a carbon-to-carbon double bond which takes part in radical, cationic, or anionic addition polymerization to give a high polymer. The term "organic group" is used in the present specification to mean any and all groups that contain 1 to 40 carbon atoms, may contain hydrogen, oxygen, nitrogen, sulfur, phosphorus, and/or halogen in addition to carbon, and meets the following requirements (a) and/or (b).

(a) Hydrocarbon groups in which hydrogen atoms are optionally substituted by —OH, —C≡N, —NH₂, —SO₃H, halogen, —COOH, —CSSH, —COSH, —COZ, or —CSZ (Z is halogen) and the carbon skeletons may be straight-chain, branched, alicyclic or aromatic or mixtures thereof.

(b) Groups corresponding to at least one of the above-mentioned hydrocarbon groups linked to at least one of the characteristic groups mentioned below, including groups which may be written as —BA or —ABA, wherein A is a hydrocarbon group and B is a characteristic group or groups. The characteristic group B may be exemplified by

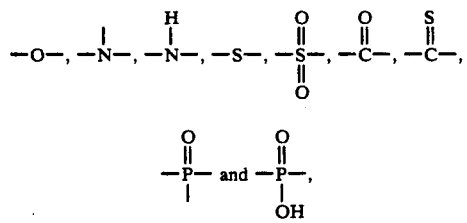

or composites of such characteristic groups, such as

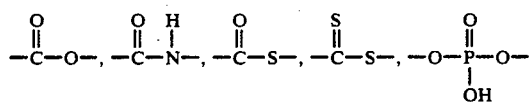

and so on.

It should be understood that where the compound of formula [I] has two or more groups which may be represented by

one of such groups is the group

in formula [I], with the other occurring in the organic group R₁.

It should also be understood that while any carbothioic acid may exist in the following tautomeric forms, all the carbothioic acids are shown in the thio, form in the present specification in accordance with the practice followed by Y. Hirabayashir T. Mazume, *Bull. Chem. Soc. Jpn.*, 38, 171 (1965); W. W. Crouch, *J. Am. Chem. Soc.*, 74, 2926 (1952); and R. Mecke, H. Spiesecke, *Chem. Ber.*, 89, 1110 (1956).

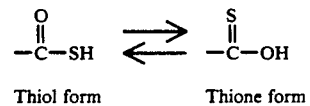

Thiol form    Thione form

The first group of compounds of general formula [I] comprises the following carbothioic acids. Thus, in general formula [I], $X_1$ is an oxygen atom, $R_1$ is an organic group of the general formula

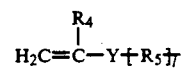

wherein $R_4$ is a hydrogen atom or a methyl group; $R_5$ is an organic group of 1 to 40 carbon atoms; Y is —COO—, —OOC—, —CONH—R —COS—, —SOC—, —S— or

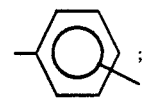

and l is 0 or 1; and $R_2$ is a mercapto group.

Therefore, the structural formula of these compounds is as follows:

$$H_2C=\underset{R_4}{C}-Y\!\!+\!\!R_5\!\!+\!\!_l\overset{O}{\underset{\|}{C}}-SH. \qquad (A)$$

In these carbothioic acids, the moiety containing the olefinic double bond is any of acryloyloxy, methacryloyloxy, vinyloxycarbonyl, isopropenyloxycarbonyl, acryloylamino, methacryloylamino, acryloylthio, methacryloylthio, vinylthiocarbonyl, isopropenyl,thiocarbonyl, vinylthio, isopropenylthio, vinylphenyl or isopropenylphenyl, and $R_1$ is an organic group containing at least one such olefinic double bond.

The second group of compounds of general formula [I] comprises the following carbodithioic acids or halides thereof. In general formula [I], $X_1$ is a sulfur atom; $R_1$ is an organic group of the general formula

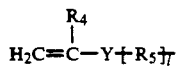

wherein $R_4$ is a hydrogen atom or a methyl group; $R_5$ is an organic group of 1 to 40 carbon atoms; Y is —COO—, —OOC—, —CONH—, —COS—, —SOC—, —S— or

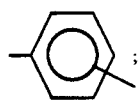

and l is 0 or 1; and $R_2$ is a mercapto group or a halogen atom.

Therefore, the structural formula of these compounds is as follows:

 (B)

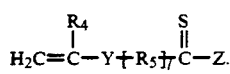 (C)

In these carbodithioic acids and halides thereof, $R_1$ and Z are the same as that defined for the abovementioned first group of compounds.

The third group of compounds of general formula [I] comprises the following thiocarboxylic acid derivatives.

In the general formula [I], $X_1$ is a sulfur atom; $R_1$ is an organic group of the general formula

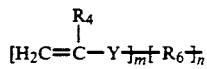

wherein $R_4$ is a hydrogen atom or a methyl group; $R_6$ is an organic group of 1 to 40 carbon atoms; Y is —COO—, —OOC—, —CONH—, —COS—, —SOC—, —S—or

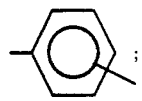

m and n each are 0 or 1 and m+n≧1; $R_2$ is —OR$_3$ or —SR$_3$; and $R_3$ is an organic group of the general formula

wherein $R'_4$ is the same as $R_4$; $R_6'$ is the same as $R_6$; Y' is the same as Y; m' and n' each are 0 or 1; n'+m'≧1; and m+m'≧1.

Therefore, the structural formula of these compounds is as follows.

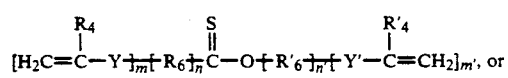 (D)

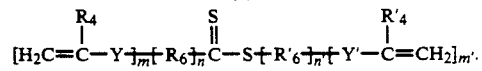 (E)

In these thiocarboxylic acid derivatives, the moiety containing the olefinic double bond is any of acryloyloxy, methacryloyloxy, vinyloxycarbonyl, isopropenyloxycarbonyl, acryloylamino, methacryloylamino, acryloylthio, methacryloylthio, vinylthiocarbonyl, isopropenylthiocarbonyl, vinylthio, isopropenylthio, vinylphenyl or isopropenylphenyl, and at least one of $R_1$ and $R_3$ is an organic group having the above-mentioned olefinic double bond. The thiocarboxylic acid derivatives which can be used in accordance with the present invention include the corresponding esters, acid anhydrides and those containing disulfide bonds as mentioned below in the following list of exemplary compounds.

The following is a list of compounds which may be used in the practice of the present invention.

Examples of Carbothioic Acids

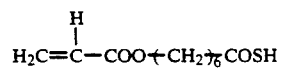

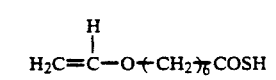

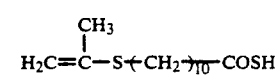

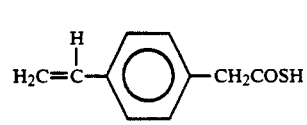

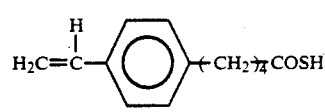

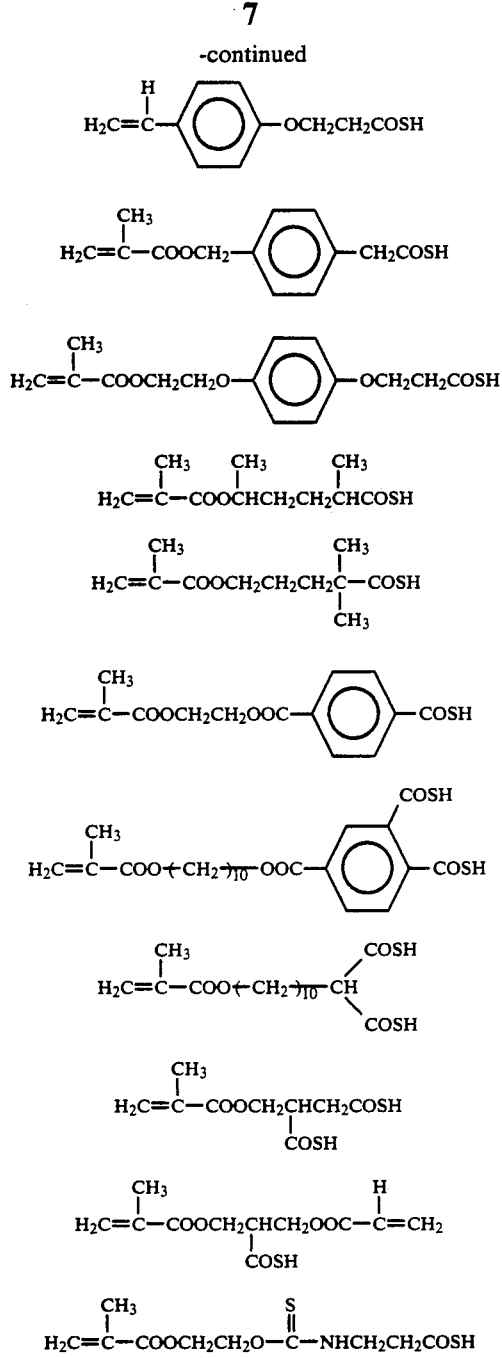
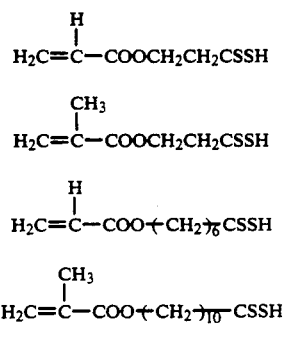
Examples of Carbodithioic Acids and Halides Thereof
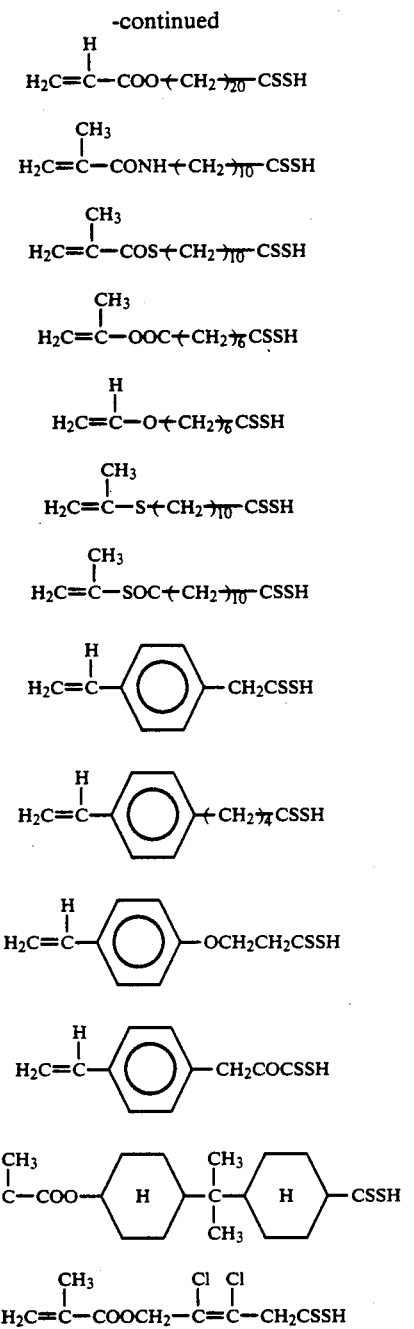
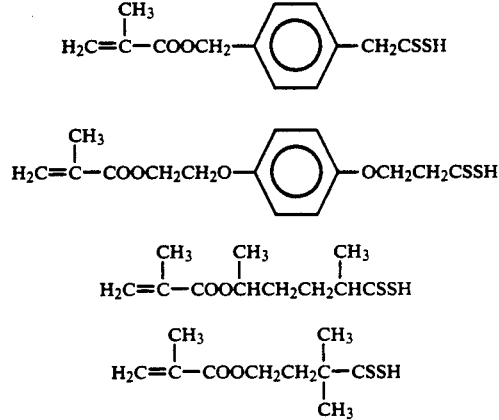

[Chemical structures of methacrylate-based thiocarboxylic acid derivatives]

Examples of Thiocarboxylic Acid Derivatives

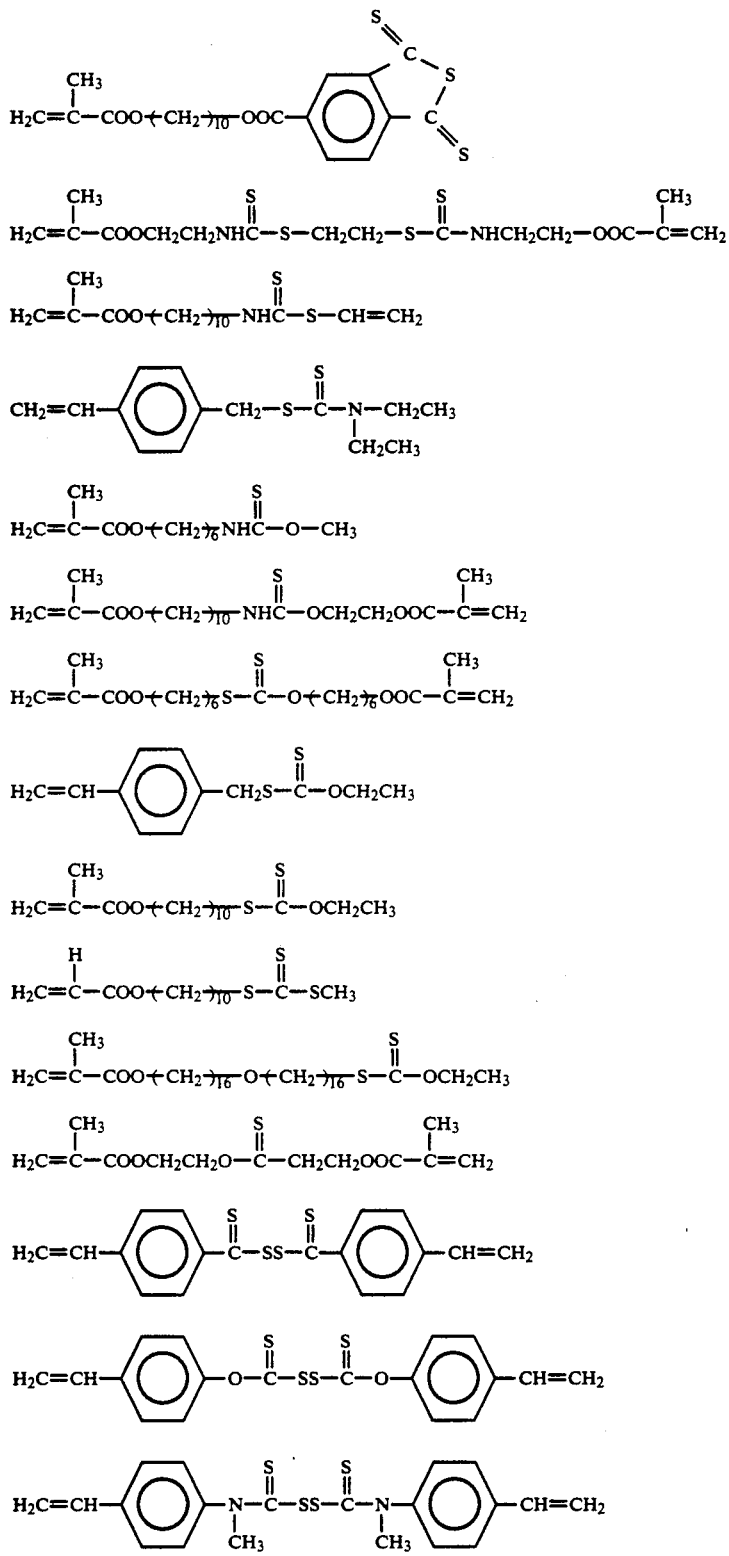

The foregoing compounds to be used as adhesive components in the present invention can be synthesized by the processes described in, for example, New Experimental Chemistry, Vol. 14 (Maruzen, 1977-1978), The Chemistry of Carboxylic Acids and Esters (John Wiley & Sons, 1969), The Chemistry of Cyanates and Their Thio Derivatives (John Wiley & Sons, 1977), and Comprehensive Organic Chemistry, Vol. 3 (Pergamon Press, 1979).

The adhesive composition of the present invention may be constituted by one of the following procedures, (1) or (2), using the compound or compounds described hereinbefore. As the solvent, those which are either copolymerizable or non-copolymerizable with said polymerizable compounds can be employed.

(1) The present compound is dissolved in a solvent which is non-copolymerizable with it, to prepare an adhesive composition. As examples of such solvents, there may be mentioned volatile organic solvents having boiling points not higher than 2500° C., such as methanol, ethanol, 2-ethylbutanol, acetone, methyl ethyl ketone, diethyl ketone, ethyl ether, n-butyl ether, 1,4-dioxane, tetrahydrofuran, ethyl acetate, toluene, xylene, p-cymene, hexane, octane, methylene chloride, 1,2-dichloroethane, 1,1,2,2-tetrachloroethane, etc., water and mixtures thereof. The concentration of the compound may range from 0.0001 to 99 percent by weight, preferably 0.001 to 50 percent by weight, based on the total weight of the compound and solvent. If necessary, a polymerization initiator and/or other co-polymerizable monomer can be added.

(2) The present compound is dissolved in a copolymerizable monomer which is described hereinbelow. The concentration of the present compound, based on the total weight of the compound and comonomer, may range from 0.005 to 99 percent by weight, and if necessary, a filler and/or a polymerization initiator is added. The adhesive composition can also be obtained by adding the present compound to an ordinary adhesive agent which consists of a monomer and an initiator and may contain a filler. In such cases, the concentration of the present compound may be in the range of 0.005 to 99 percent by weight, based on the total weight of the present compound and comonomer. Moreover, the above-mentioned two types of solvents may be used in combination.

The adhesive composition of the present invention can be used not only as an adhesive in the usual manner but also as a primer for other adhesives. For use as a primer, the adhesive composition of the present invention is, for example, applied to the surface of a metal and then, the ordinary adhesive or composite resin is applied for bonding the metal to the other material.

The fact that the present compound improves the bond strength even when used in a trace amount, is probably attributable to the monomolecular adsorption of the compound on the metal surface. This effect is not adversely affected by solvent washing of the primer-coated surface.

The adhesive composition of the present invention is preferably used as a primer, and as mentioned above, the adherend surface coated with this primer accepts the conventional adhesive, preferably an acrylic monomer-containing adhesive, to provide a firm bond.

The adhesive of the present invention exhibits excellent water resistance, and when the bonded specimen is kept in water at room temperature, no prominent decrease occurs in bond strength over several months.

The copolymerizable monomer to be used as the solvent for the present compound is preferably a (meth-)acrylic acid ester [the term "(meth)acrylic acid ester" means either or both of methacrylate and acrylate], such as methyl methacrylate, 2-hydroxyethyl methacrylate, ethylene glycol dimethacrylate, triethylene glycol dimethacrylate, neopentyl glycol dimethacrylate, 2,2-bis[4-(3-methacryloyloxy-2-hydroxypropoxy)-phenyl]propane (Bis-GMA), 2,2-bis(methacryloyloxyethoxyphenyl)propane, trimethylolethane triacrylate, pentaerythritol tetraacrylate, 4-(2-methacryloyloxyethyl) trimellitate, 4-methacryloyloxyethyl trimellitate anhydride, bis(2-methacryloyloxyethyl) hydrogen phosphate, 2-methacryloyloxyethyl phenyl hydrogen phosphate, 6-methacryloyloxyhexyl dihydrogen phosphate, 10-methacryloyloxydecyl dihydrogen phosphate, tris(2-methacryloyloxyethyl) phosphate, 2-(dimethylamino)ethyl (meth)acrylate and so on.

As mentioned above, a polymerization initiator is usually incorporated in the adhesive composition of the present invention. As examples of such polymerization initiators, there may be mentioned benzoyl peroxide-aromatic tertiary amine systems, peroxides such as cumene hydroperoxide, tributylborane, aromatic sulfinic acid or its salt -aromatic secondary or tertiary amine-acyl peroxide systems. In addition, there may be used photopolymerization initiators such as camphorquinone and camphorquinone-tertiary amine, camphorquinone-aldehyde, camphorquinone-mercaptan and other systems.

When the adhesive composition is to be used as a primer and a different adhesive agent is applied on the primer, it is not essential to incorporate such an initiator in the composition of the present invention, because the polymerization initiator contained in the other adhesive agent will migrate to induce a polymerization.

If necessary, the adhesive composition of the present invention may further contain inorganic fillers such as quartz, glass, hydroxyapatite, calcium carbonate, barium sulfate, titanium dioxide, zirconium oxide, etc., and powders of polymers such as polymethyl methacrylate, polystyrene, polyvinyl chloride and so on.

Among adherend metals to which the adhesive composition of the present invention is applicable are noble metals such as gold, platinum, palladium, silver, ruthenium, rhodium, osmium, iridium, etc. and a broad range of base metals such as iron, nickel, cobalt, copper, zinc, tin, aluminum, titanium, vanadium, chromium, manganese, zirconium, molybdenum, cadmium, indium, antimony and so on. The adhesive of the present invention is also applicable to metal oxides such as aluminum oxide, titanium oxide, zirconium oxide, and further to ceramic materials containing such metal oxides.

Owing to its excellent water-resistant adhesiveness to metals and particularly to noble metals, the adhesive composition of the present invention finds application with great advantage in the dental field. For example, it is very useful as an adhesive for bonding a noble metal casting such as an inlay, crown, bridge or the like to a tooth, an adhesive for preparing a prosthetic appliance simulating a natural tooth by bonding a resin or ceramic veneer layer to the surface of a noble metal frame, or an adhesive for bonding cast parts of noble metal into a single complete assembly.

It should, however, be understood that the adhesive composition of the present invention is not only useful in the dental field but also finds application in any other industrial area where bonding of metals or metal oxides is practiced.

Having generally described the present invention, a further understanding can be obtained by reference to certain specific examples which are provided herein for purposes of illustration only and are not intended to be limiting unless otherwise specified.

EXAMPLES

Production of the Carbothioic Acid

Production Example 1.

In 150 ml of 90% ethanol was dissolved 9 g of potassium hydroxide, and the solution was saturated with hydrogen sulfide with ice-cooling. Then, 30 g of 11-bromoundecanoyl chloride was added dropwise with constant stirring to the mixture. After completion of the dropwise addition, the temperature was allowed to return to room temperature and the reaction mixture was further stirred for 1 hour. After the insoluble matter was filtered off, the solvent was distilled off under reduced pressure and the residue was dissolved in 150 ml of cold water. Then, neutral impurities were extracted with benzene. The aqueous solution was acidified with 6N-hydrochloric acid and the liberated organic matter was extracted with ether. This ether layer was washed with water and dried over anhydrous sodium sulfate and the ether was distilled off under reduced pressure to recover 18 g of 11-bromoundecanethioic acid. A mixture of 9.5 g of silver methacrylate, 50 ml of ether, and 15 g of the above 11-bromoundecanethioic acid was refluxed for 72 hours, and after cooling, the insoluble matter was filtered off. The solvent was then distilled off under reduced pressure and the residue was purified by chromatography. 7.2 g of a solid compound were obtained. By elemental analysis and NMR, the above compound was identified to be 11-methacryloyloxyundecanethioic acid.

Production of the Carbodithioic Acid

Production Example 2.

A three-necked flask fitted with a dropping funnel, stirrer and reflux condenser was charged with 5 g of magnesium and 100 ml of ether. Then, a solution of 45 g of 10-bromo-1-decene in 200 ml of ether was added via the dropping funnel to prepare a Grignard reagent. Under cooling in an ice bath, 15 g of carbon disulfide was added dropwise with stirring. After completion of the dropwise addition, the mixture was stirred in an ice bath for 24 hours, and then ice-water was added to the mixture. The aqueous layer was acidified with dilute hydrochloric acid, and the liberated organic matter was extracted with ether. This ether layer was washed with water and dried over anhydrous sodium sulfate, and the ether was distilled off under reduced pressure to recover 26 g of 10-undecenedithioic acid. In 100 ml of n-hexane were dissolved 22 g of 10-undecenedithioic acid and 0.2 g of benzoyl peroxide and then, 14 g of dry hydrogen bromide gas was bubbled into the solution at 0° C. for 2 hours. Thereafter, the temperature of the mixture was allowed to return to room temperature, and the mixture was allowed to stand for 12 hours. The n-hexane was then distilled off to recover 18 g of 11-bromoundecanedithioic acid. A mixture of 9.5 g of silver methacrylate, which was prepared from methacrylic acid, sodium hydroxide, and silver nitrate, 60 ml of ether, and 16 g of the thus-obtained 11-bromoundecanedithioic acid was refluxed for 72 hours with heating, and the insoluble matter was filtered off after cooling. The solvent was then distilled off from the solution under reduced pressure and the residue was purified by chromatography. 9.2 g of a solid compound were obtained. By elemental analysis and NMR, this compound was identified to be 11-methacryloyloxyundecanedithioic acid.

Production of the Carbodithioic Acid Chloride

Production Example 3.

A 50 cc round-bottomed flask was charged with 5 g of 11-methacryloyloxyundecanedithioic acid, 6 g of thionyl chloride, 0.1 g of pyridine, and a trace amount of cuprous chloride, and the mixture was refluxed at 80° C. until the evolution of gases subsided. Then, this flask was connected to a vacuum distillation apparatus, and the low-boiling fraction was distilled off. The residue was then purified by chromatography to recover 3.2 g of a liquid compound. By elemental analysis and NMR, this liquid compound was identified as 11-methacryloyloxyundecanethioic acid chloride. In the present invention, this compound is named as the carbodithioic acid chloride.

Production of the Carbodithioic Acid Ester

Production Example 4.

In a solution of 6 g of potassium hydroxide in 50 ml of methanol was dissolved 20 g of 10-undecenedithioic acid, an intermediate compound in Production Example 2, and 22 g of 10-bromo-1-decene was added dropwise under cooling in an ice bath. The mixture was stirred for 6 hours. The insoluble matter was filtered off, and the solvent was then distilled off to recover 9-decenyl 10-undecenedithioate. In 30 ml of n-hexane were dissolved 8 g of the above 9-decenyl 10-undecenedithioate and 0.05 g of benzoyl peroxide, and then, 4 g of dry hydrogen bromide gas was bubbled into the solution at 0° C. for 1.5 hours. The temperature of the mixture was allowed to return to room temperature, and the mixture was then allowed to stand for 12 hours. The n-hexane was distilled off, and the residue was purified by column chromatography. 7.5 g of 10-bromodecyl 11-bromoundeconedithioate were obtained.

A mixture of 4 g of silver methacrylate, 20 ml of ether, and 5 g of the thus-obtained 10-bromodecyl 11-bromoundecanedithioate was refluxed for 96 hours, and after cooling, the insoluble matter was filtered off. The solvent was then distilled off from the solution under reduced pressure, and the residue was purified by chromatography. 2.8 g of a solid compound were thus obtained. By elemental analysis and NMR, the above compound was identified to be 10-methacryloyloxydecyl 11-methacryloyloxyundecanedithioate.

Adhesives

Examples 1 through 25 and Comparative Examples 1 through 3.

Using the 25 different compounds listed in Table 1 and the conventional compounds mentioned hereinbefore, viz. N-(4-mercaptophenyl)methacrylamide and 3-(isopropenylthiocarbonylthio) propyltrimethoxysilane, the adhesive effects on noble metals were evaluated.

Each of the above compounds was dissolved in toluene at a concentration of 1 percent by weight to give a primer. Then, a pure gold plate ($10 \times 10 \times 1$ mm) (reinforced with a 4 mm thick stainless steel plate on the reverse side), a dental gold-silver-palladium alloy [Castwell ®, GC Dental Industrial Corp., Au=12%, Ag≧45%, Pd=20%, $10 \times 10 \times 1$ mm, reinforced in the same manner as above], and a dental gold-platinum-palladium alloy [Degudent Universal, Mitsubishi Metal Corp., Au=77%, Pt=10%, Pd=9%, $10 \times 10 \times 1$ mm, reinforced in the same manner as above] were polished in advance with a silicon carbide abrasive paper (1000 grit) and coated with each of the above toluene solutions using a brush. After 1 minute, the coated surface was washed with pure toluene so as to leave a monomolecular layer adsorbed on the metal surface. Then, an adhesive tape with an aperture 5 mm in diameter was applied to the above surface to prepare an adherend surface. On the other hand, a round bar of SUS 304, 7 mm in diameter and 25 mm long, was provided, and the end face of the bar was sand-blasted with alumina abrasive having a particle diameter of 50 μm. On this end face was set up a paste of dental adhesive (Panavia® Kuraray Co., Ltd.) which comprised 100 parts by weight of methacrylic acid ester, 3 parts by weight of sodium sulfinate-benzoyl peroxide-tertiary amine polymerization initiator, and 320 weight parts of silanated inorganic filler, and the end face of the bar carrying the paste was pressed against said adherend surface for bonding. After one hour, the testpiece was immersed in water at 37° C. After 24 hours of immersion, the tensile bond strength was measured using a universal materials testing machine (Instron Ltd.) at a crosshead speed of 2 mm/minute. The mean value of the results for 8 testpieces is shown in Table 1.

| | Adhesive component of primer | Bond strength to pure gold $(Kg/cm^2)$ | Bond strength to Castwell $(Kg/cm^2)$ | Bond strength to Degudent Universal $(Kg/cm^2)$ |
|---|---|---|---|---|
| Example 1 | $H_2C=C(CH_3)-COOCH_2CH_2COSH$ | 260 | 271 | 308 |
| Example 2 | $H_2C=C(CH_3)-COO(CH_2)_{10}COSH$ (Compound of Production Example 1) | 342 | 353 | 380 |
| Example 3 | $H_2C=C(CH_3)-COOCH_2CH_2CSSH$ | 302 | 312 | 320 |
| Example 4 | $H_2C=C(H)-COO(CH_2)_6CSSH$ | 348 | 366 | 379 |
| Example 5 | $H_2C=C(CH_3)-COO(CH_2)_{10}CSSH$ (Compound of Production Example 2) | 360 | 378 | 389 |
| Example 6 | $H_2C=C(CH_3)-CONH(CH_2)_{20}CSSH$ | 365 | 372 | 391 |
| Example 7 | $H_2C=C(H)-COS(CH_2)_{10}CSSH$ | 366 | 387 | 383 |
| Example 8 | $H_2C=C(H)-OOC(CH_2)_6CSSH$ | 320 | 335 | 346 |
| Example 9 | $H_2C=C(H)-SOC(CH_2)_{10}CSSH$ | 352 | 361 | 373 |
| Example 10 | $H_2C=C(H)-C_6H_4-(CH_2)_4CSSH$ | 351 | 390 | 382 |
| Example 11 | $H_2C=C(CH_3)-COO-C_6H_{10}-C(CH_3)_2-C_6H_{10}-CSSH$ | 346 | 359 | 374 |
| Example 12 | $H_2C=C(CH_3)-COOCH_2-C(Cl)=C(Cl)-CH_2CSSH$ | 328 | 330 | 349 |
| Example 13 | $H_2C=C(CH_3)-COO(CH_2)_{10}-O-CSSH$ | 358 | 355 | 374 |
| Example 14 | $H_2C=C(CH_3)-COO(CH_2)_{10}-S-CSSH$ | 361 | 380 | 366 |

-continued

| | Adhesive component of primer | Bond strength to pure gold (Kg/cm$^2$) | Bond strength to Castwell (Kg/cm$^2$) | Bond strength to Degudent Universal (Kg/cm$^2$) |
|---|---|---|---|---|
| Example 15 | $H_2C=CH-C_6H_4-CH_2COCSSH$ | 342 | 357 | 358 |
| Example 16 | $H_2C=C(CH_3)-COO(CH_2)_{10}-OOC-C_6H_3(CSSH)_2$ | 368 | 395 | 406 |
| Example 17 | $H_2C=C(CH_3)-COOCH_2CH_2O-C(=S)-CH_2CH_2CSSH$ | 356 | 364 | 379 |
| Example 18 | $[H_2C=C(CH_3)-COOCH_2CH_2]_2N-CSSH$ | 348 | 338 | 371 |
| Example 19 | $H_2C=C(CH_3)-COOCH_2CHCH_2OCH_2CHCH_2OCH_2CHCH_2OOC-C(CH_3)=CH_2$ with pendants $H_2C=C(CH_3)-COO$, $CSSH$, $OOC-C(CH_3)=CH_2$ | 314 | 306 | 334 |
| Example 20 | $H_2C=C(CH_3)-COO(CH_2)_{10}-CSCl$ (Compound of Production Example 3) | 337 | 368 | 361 |
| Example 21 | $H_2C=C(CH_3)-COO(CH_2)_{10}-C(=S)-S(CH_2)_{10}OOC-C(CH_3)=CH_2$ (Compound of Production Example 4) | 295 | 306 | 311 |
| Example 22 | $H_2C=C(CH_3)-COO(CH_2)_{10}-S-C(=S)-OCH_2CH_3$ | 278 | 290 | 302 |
| Example 23 | $H_2C=C(CH_3)-COO(CH_2)_{16}-O(CH_2)_{16}-S-C(=S)-OCH_2CH_3$ | 282 | 301 | 296 |
| Example 24 | $H_2C=C(CH_3)-COO(CH_2)_{10}-C(=S)-S-C(=S)(CH_2)_{10}-OOC-C(CH_3)=CH_2$ | 319 | 316 | 348 |
| Example 25 | $H_2C=C(CH_3)-COO(CH_2)_{10}-NH-C(=S)-OCH_2CH_2OOC-C(CH_3)=CH_2$ | 270 | 307 | 316 |
| Comparative Example 1 | N-(4-Mercaptophenyl)methacrylamide | 234 | 243 | 173 |
| Comparative Example 2 | 3-(Isopropenylthiocarbonylthio)propyltrimethoxysilane | 202 | 217 | 149 |
| Comparative Example 3 | None | 171 | 151 | 128 |

EXAMPLES 26 AND 27 AND COMPARATIVE EXAMPLE 4

In the same manner as Example 1, a Castwell ® adherend was coated with a 1% toluene solution of the compound used in Example 2 and after a lapse of 1 minute, the coated surface was washed with pure toluene. Then, a stainless steel bar was adhered using Panavia EX ® (Kuraray Co., Ltd.) to prepare a testpiece (Example 26). Similarly, a testpiece (Example 27) was prepared with the compound used in Example 5. On the other hand, as a control, a testpiece (Comparative Example 4) was prepared by bonding a stainless steel bar directly to a Castwell® adherend with Panavia EX ® instead of the adhesive composition of the present invention. After 1 hour, for 1/2he evaluation of water resistance, these testpieces were immersed in water at 37° C. for 24 hours. Each testpiece was transferred into water at 70° C., in which it was allowed to remain for 10 days. Thereafter, the tensile bond strength of each testpiece was measured in the same manner as described in Example 1. As a result, the mean bond strength of Example 26 was 283 kg/cm² and that of Example 27 was 340 kg/cm², in contrast to the mean bond strength of 31 kg/cm² for Comparative Example 4.

EXAMPLES 28 AND 29 AND COMPARATIVE EXAMPLE 5

A two-packages adhesive consisting of the following pastes, A and B, was prepared.

| Paste A | |
| --- | --- |
| Bis-GMA | 12.5 Parts by weight |
| Triethylene glycol dimethacrylate | 12.5 |
| Adhesive component of Example 2 | 0.1 |
| N,N-Diethanol-p-toluidine | 0.5 |
| Silanated quartz powder | 74.5 |
| Paste B | |
| Bis-GMA | 12.5 Parts by weight |
| Triethylene glycol dimethacrylate | 12.5 |
| Benzoyl peroxide | 0.5 |
| Silanated quartz powder | 74.5 |

The above pastes, A and B, were mixed in equal parts by weight to prepare an adhesive (Example 28), and by the bonding procedure described in Example 1 and by the bonding procedure described in Example 1 (provided that a primer was not applied), a dental alloy [Herador H ®, Heraeus Edulmetalle GmbH, West Germany; Au=79%, Pt=10%, Pd=8%] adherend polished with silicon carbide abrasive paper (1000 grit) was bonded to a sand-blasted stainless steel bar with the aboveprepared adhesive. The adhesive testpiece was immersed in water at 37° C. for 24 hours and the tensile bond strength was measured. As a result, an adhesive failure occurred between the gold alloy and the adhesive, and the mean strength (n=8) was 222 kg/cm².

A similar experiment was performed with the adhesive component of Example 5 in lieu of that of Example 2. In this case (Example 29), the mean bond strength was 286 kg/cm².

On the other hand, a paste A' was prepared by omitting the adhesive component of Example 2 from the composition of paste A, and in the same manner as Examples 28 and 29, a bonding experiment was carried out in the combination of A'+B (Comparative Example 5). As a result, an adhesive failure occurred between the gold alloy and the adhesive, and the mean bond strength was 106 kg/cm².

EXAMPLE 30

A powder-liquid mixture adhesive of the following components, C and D, was prepared.

| Powder C | |
| --- | --- |
| Silanated silica powder | 100 Parts by weight |

| -continued | |
| --- | --- |
| Sodium benzenesulfinate | 0.4 |
| N,N-Diethanol-p-toluidine | 0.5 |
| Liquid D | |
| Bis-GMA | 50 Parts by weight |
| 1,6-Hexanediol dimethacrylate | 39 |
| 10-Methacryloyloxydecyl dihydrogen phosphate | 10 |
| Adhesive component of Example 5 | 1 |
| Benzoyl peroxide | 1 |

Using an adhesive paste prepared by blending 1 g of liquid D with 3 g of powder C, a sandblasted stainless steel bar was bonded to a dental alloy [Herador H ®] adherend polished with silicon carbide abrasive paper (1000 grit) by the same procedure as in Example 1 (provided, however, that a primer was not applied). The adhesion testpiece was immersed in water at 37° C. for 24 hours, and the tensile bond strength was measured. As a result, a cohesive failure of the adhesive occurred, and the means bond strength (n=8) was 328 kg/cm².

EXAMPLE 31

A disk (4 mm in diameter, 3 mm thick) was cast from Degudent Universal ®, a dental alloy, and the surface of the disk was polished with silicon carbide abrasive paper (1000 grit) to prepare an adherend (A). Meanwhile, the labial surface enamel of a human maxillary central incisor was polished with the same abrasive paper as above to prepare a flat surface, and this surface was further subjected to acid etching with a 40% aqueous solution of phosphoric acid, rinsed and dried to provide an adherend (B).

The adherend (A) was coated with the primer of Example 2, and after evaporation of the toluene, it was bonded to the adherend (B) using Panavia EX ®, and the specimens were obtained. After immersion of the specimens in water at 37° C. for a half year, a mean value of tensile bond strength of the 8 specimens was 181 Kg/cm², and the adhesive failure occurred at the interface between enamel and Panavia EX.

Obviously, numerous modifications and variations of the present invention are possible in light of the above teachings. It is therefore to be understood that within the scope of the appended claims, the invention may be practiced otherwise than as specifically described herein.

What is new and desired to be secured by letters patent of the United States is:

1. A method of bonding a metal or alloy to another material, comprising:
    (i) applying an adhesive composition to said metal or alloy to obtain an adhesive coated metal or alloy; and
    (ii) contacting said another material with said adhesive coated metal;
wherein said adhesive composition comprises a polymerizable thiocarboxylic acid or derivative thereof of the formula:

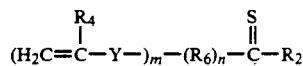

wherein $R_4$ is hydrogen or methyl; $R_6$ is a hydrocarbon group of 1 to 40 carbon atoms which can be substituted with —OH, —C≡N, —NH₂, —SO₃H, halogen, —COOH, —CSSH or —COSH; Y is —COO—, —OOC—, —CONH—, —COS—, —SOC—, —S— or

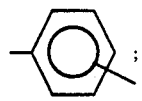

$R_2$ is —SH or —SR$_3$, where R$_3$ is a hydrocarbon group of the formula

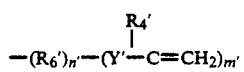

wherein $R_4'$ is the same as $R_4$; $R_6'$ is the same as $R_6$; $Y'$ is the same as Y;

with the proviso that when Y is —COO—, —OOC—, —CONH—, —COS—, —SOC— or —S—, n is 1; when Y is

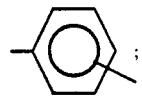

n is 0 or 1; when $R_2$ is —SH, then m is 1; that when $R_2$ is —SR$_3$, m is 0 or 1; that m+n≧1; that when Y' is —COO, —OOC, —CONH—, —COS—, —SOC— and —S—, $n^1$ is 1; that when Y' is

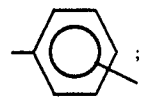

n' is 0 is 1; that m' is 0 or 1; m'+n'≧1; and m+m≧1.

* * * * *